United States Patent [19]

Rosenthal

[11] Patent Number: 4,627,008

[45] Date of Patent: Dec. 2, 1986

[54] OPTICAL QUANTITATIVE ANALYSIS USING CURVILINEAR INTERPOLATION

[75] Inventor: Robert D. Rosenthal, Gaithersburg, Md.

[73] Assignee: Trebor Industries, Inc., Gaithersburg, Md.

[21] Appl. No.: 603,821

[22] Filed: Apr. 25, 1984

[51] Int. Cl.⁴ .................. G06F 15/20; G01N 21/00; G01J 3/48

[52] U.S. Cl. .................................. 364/550; 364/498; 356/416; 250/338

[58] Field of Search .............. 364/550, 571, 525, 526, 364/498, 497; 250/338, 341, 343, 345; 356/416, 418

[56] References Cited

U.S. PATENT DOCUMENTS

| | | | |
|---|---|---|---|
| 3,776,642 | 12/1973 | Anson et al. | 356/188 |
| 3,828,173 | 8/1974 | Knepler | 364/498 |
| 3,861,788 | 1/1975 | Webster | 359/315 |
| 4,286,327 | 8/1981 | Rosenthal et al. | 364/498 |
| 4,404,642 | 9/1983 | Rosenthal | 364/498 X |
| 4,466,076 | 8/1984 | Rosenthal | 364/498 X |
| 4,498,778 | 2/1985 | White | 364/571 X |

Primary Examiner—Edward J. Wise
Attorney, Agent, or Firm—Bernard, Rothwell & Brown

[57] ABSTRACT

In the quantitative analysis of a sample by computing constituents from optical absorptivity data at different wavelengths, optical absorptivity data values for selected nominal wavelengths are obtained by curvilinear interpolation from measured optical absorptivity data values obtained by use of narrow band width filters. The computed optical data values are utilized to compute percentage constituents by means of algorithms which may include one or more first or second derivatives.

18 Claims, 7 Drawing Figures

OPTICAL QUANTITATIVE ANALYSIS USING CURVILINEAR INTERPOLATION

BACKGROUND OF THE INVENTION

1. Field of the Invention

The present invention relates to the quantitative analysis of samples such as grains, fruit, chemicals, and other materials by measuring the absorptivity of the samples to electromagnetic radiation such as near infrared radiation.

2. Description of the Prior Art

As exemplified in U.S. Pat. Nos. 3,776,642, 3,828,173, 3,861,788 and 4,286,327, the prior art contains a number of apparatus and processes for analyzing samples such as grains for moisture, protein and oil content utilizing near infrared quantitative analysis wherein readings of the absorptivity of the samples to near infrared radiation at several selected narrow bandwidth wavelengths are obtained and processed by a computer to determine the quantity of one or more constituents of the samples. These readings can be obtained by various arrangements of an infrared source or sources such as infrared emitting diodes (IREDs) or lamps, filters, and an infrared detector or detectors such as silicon photocells or lead sulphide photodetectors. The filters may be stationary in branch optical paths from respective IREDs or to respective detectors or on a tilting paddle wheel or a rotating disc for passing through a single optical path between a source and a detector. Each detected signal is generally amplified logarithmically or converted to a logarithmic scale in a computer to obtain an optical data reading of absorptivity OD which is equal to log $1/T$ where T is the percent of infrared energy transmitted at the selected wavelength or which is equal to log $1/R$ where R is the percent of infrared energy reflected at the selected wavelength. Alternatively, the absorptivity or optical data values OD need not be logarithmic and can be equal to $1/T$ or $1/R$ or some other function of transmissivity or reflectivity. The optical data readings are processed in a computer to obtain the percentage (%) of each constituent in accordance with an algorithm or formula such as one of the following well known formulas:

$$\% = K_o + K_1 OD_1 + K_2 OD_2 + \cdots + K_n OD_n \quad (1)$$

$$\% = K_o + K_1 dOD_1 + K_2 dOD_2 + \cdots + K_n dOD_n \quad (2)$$

$$\% = K_o + K_1 \frac{dOD_1}{dOD_c} \quad (3)$$

$$\% = K_o + K_1 d^2 OD_1 + K_2 d^2 OD_2 + K_n d^2 OD_n \quad (4)$$

$$\% = K_o + K_1 \frac{d^2 OD_1}{d^2 OD_c} \quad (5)$$

The formula (1) is a multiple linear equation wherein the constants $K_o$-$K_n$ are determined by multiple regression techniques, i.e., optical readings are obtained from the sources, filters and detectors of the instrument being constructed for a representative number of grain samples which have been accurately analyzed by laboratory test equipment, and the optical readings and previously measured percentages are utilized to calculate sets of $K_o$-$K_n$ values for the respective moisture, oil and protein content using a conventional regression algorithm in a digital computer. These sets of $K_o$-$K_n$ values are then programmed into the analyzing instrument being constructed so that the instrument can directly compute the constituent percentages (moisture, oil, protein, etc.) from optical data readings.

Formula (2) is similar to the Formula (1) except that the first derivatives of the optical data readings $OD_1$–$OD_n$ are utilized. In the computer, the first derivatives are approximated by the difference between two adjacent optical readings such as in the formula:

$$dOD_1 = OD_1 - OD_2 \quad (6)$$

Formula (2) has the advantage that accurate percentages can be constituted utilizing less optical data terms and the derivative terms provide correction for voltage drifts in instrument readings.

Formula (3) computes a normalized first derivative by dividing the derivative of a reading at one selected point 1 by derivatives of readings at a second point C; the first and second point being selected to produce the numerator and denominator needed to calculate the desired percentage over a broad range of constituent values. These points further are selected to compensate for light-scattering and mutual interferences. Sets of values $K_o$ and $K_1$ are determined, like the values $K_o$-$K_n$ in formulas (1) and (2), by multiple regression techniques. Formula (3) may have a single first derivative term or may have several single derivative terms.

Formulas (4) and (5) are similar to Formulas (2) and (3) except that second derivatives of the optical readings are utilized; the second derivatives are derived by approximation utilizing the formula:

$$d^2 OD_1 = OD_2 + OD_3 - 2OD_1 \quad (7)$$

wherein $OD_2$ and $OD_3$ are adjacent optical readings taken at wavelengths slightly lower and slightly higher than $OD_1$.

The multiple linear equation (4) utilizing second derivatives and the equation (5) with normalized second derivative terms are more complex but provide versatile approaches enabling accurate results from fewer readings as well as improved compensation for light scattering, and mutual interferences.

In prior U.S. patent application Ser. No. 355,325, filed Mar. 8, 1982, there is described the use of a formula of the type:

$$\% = K_o + K_1 OD_1 + \cdots + K_n OD_n + K_G T_G + K_A T_A \quad (8)$$

wherein:

$T_G$ = Grain or sample Temperature
$T_A$ = Ambient Temperature
$K_G$ and $K_A$ are constants which are determined along with $K_o$-$K_n$ by multiple regression techniques including readings made at different temperatures. The inclusion of the terms $K_G T_G$ and $K_A K_A$ compensates for changes in optical data readings due to different temperatures of the grain or sample, and of the testing instrument.

Generally the desired wavelengths used in the above algorithms for analyzing various grains and other materials are well known in the art and are found in various publications. Analytical and empirical techniques are often used to optimize the selected wavelengths.

In the manufacture of infrared quantitative analytical instruments, the determination of the constants K by multiple regression techniques generally requires about ten samples for each constant to be determined. For the formula (8) where about twelve optical data terms are utilized, about one hundred fifty samples are required to calibrate the instruments. Utilization of less samples results in K values which produce inaccurate results in measuring samples which vary from the samples used in calibration. The maintenance and analytical laboratory procedures for the large number of different samples add substantially to the costs of manufacturing instruments. Thus utilization of algorithms with fewer terms, such as algorithm (5), is desirable to lower costs of maintaining and analyzing calibration samples.

The algorithms employing derivatives, and especially second derivatives, are also desirable since they produce superior results from samples which vary from the calibration samples. In use of algorithm (1) and, to a somewhat lesser degree, algorithms (2) and (3), inaccurate constituent percentages can be produced where the sample being analyzed varies from the samples used in calibration. Particularly inaccurate constituent percentages can be produced where the calibration samples are not sufficiently varied in constituents to closely cover the range of constituents in which the sample being analyzed is found. The algorithms with derivative terms, and especially second derivative terms, are much more accurate when the sample being analyzed varies from the samples used in calibration.

One problem in the manufacture of relatively low cost commercial instruments concerns the inability to obtain readings at precise wavelengths. Generally, the instruments must employ narrow band pass optical filters in order to obtain readings at the desired wavelengths. Unfortunately, the reasonably priced, commercially available narrow band pass filters have actual center wavelength responses which vary up to about ±2nm together with a similar half power band width tolerance from their nominal responses. The algorithms (2) and (3) employing fewer terms with first derivatives are more wavelength sensitive than the multiple linear equation (1) employing twelve or more terms of basic optical data readings, and the algorithms (4) and (5) employing second derivatives are even more wavelength sensitive such that the normal tolerance or variations in the available filters hinders the employment of single or low term derivative formulas in relatively low cost instruments. Expensive laboratory instrumentation such as a scanning monochrometer, can be utilized to obtain accurate wavelength information suitable for use by algorithms employing first and second derivatives. Besides being relatively expensive, the scanning monochrometers are relatively more prone to mechanical problems and failure.

Another approach to obtain accurate wavelength readings is to adjust the tilt of each narrow band pass filter in construction of the instrument. Tilting of a band pass filter causes slight shifts in the center wavelength response of the filter, thus allowing the filter to be adjusted to an accurate wavelength. The relationship between the tilt angle and center wavelength response is nonlinear, and accurate adjustment of the tilt angle to accurately tune each filter is difficult to perform.

In the "tilting filter paddle wheel" approach, a large number of readings can be made at closely spaced wavelengths. In addition to the difficulties from the nonlinearity of the tilt angles and wavelengths responses, this approach also requires accurate encoders and other precision optical and mechanical devices along with time consuming manufacturing procedures which make the cost of such instruments relatively higher.

Still another approach to overcoming the wavelength variation of filters is to sort individual filters so as to utilize only filters with the desired accurate wavelength response; however, the yield of acceptable filters is too small to render this approach practical since most of the filters would be unusable resulting in increased costs.

SUMMARY OF THE INVENTION

The present invention is summarized in an apparatus for optically obtaining a quantitative value of a wavelength variable constituent in a sample wherein optical absorptivity readings are obtained at a plurality of different wavelengths, and then curvilinear interpolation techniques are employed to compute a plurality of computed optical absorptivity values from the measured optical absorptivity values. From these computed optical absorptivity values, accurate percentages of constituents can be computed utilizing known algorithms including algorithms employing single term first and second derivatives of the optical data values.

An objective of the invention is to construct an instrument for measuring constituents of a sample utilizing optical techniques wherein the instrument can be manufactured relatively inexpensively.

Another object of the invention is to accuately compute additional optical data values of samples at wavelengths between measurement wavelengths to improve the accuracy of constituent percentage values computed from the optical data values.

One advantage of the invention is that the conventional narrow band pass optical filters which have varying wavelength responses can be utilized in quantitative optical analyzing equipment without expensive filter tilting procedures and the like.

One feature of the invention is that accurate optical data values can be obtained for optimally selected wavelengths by computerized curvilinear techniques from optical data readings obtained using narrow band pass filters with center wavelengths which may differ from instrument to instrument.

Other objects, advantages and features of the invention will be apparent from the following description of the preferred embodiments taken in conjunction with the accompanying drawings.

DESCRIPTION OF THE PREFERRED EMBODIMENTS

Figure 1:
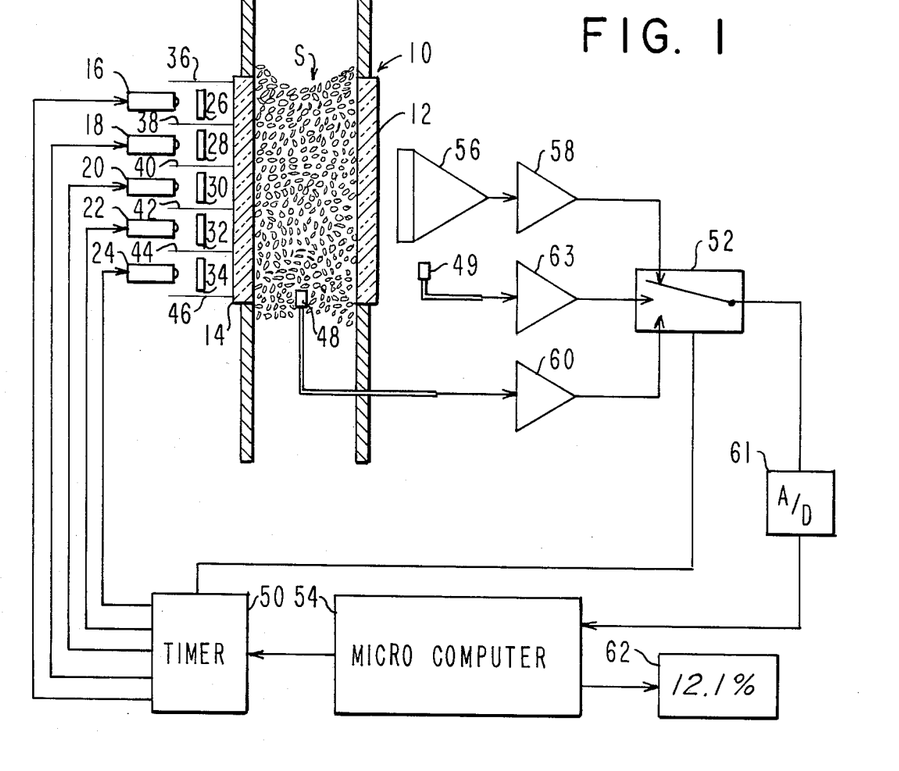
FIG. 1 is a schematic diagram of a near infrared quantitative analysis instrument in accordance with the invention.

As shown in FIG. 1, an optical quantitative analyzing instrument in accordance with the invention includes sample handling means such as a sample chamber indicated generally at 10 for containing a quantity of grain sample S. The sample chamber 10 includes opposite walls with windows 12 and 14 transparent to infrared radiation for supporting a predetermined thickness of the sample S therebetween during the measurement. A suitable gate (not shown) is positioned below the sample to hold the sample within the chamber 10 during the measurement and to release the sample S after the measurement is completed.

A plurality of infrared emitting diodes (IREDs) 16, 18, 20, 22 and 24, corresponding individual narrow band pass filters 26, 28, 30, 32 and 34, and a lens system (not shown) such as described in U.S. Pat. No. 4,379,233 are positioned over the window 14 so that light or infrared radiation from one of the IREDs passing through the corresponding filter impinges on the sample S through the window 14. Suitable shields, including baffles 36, 38, 40, 42, 44 and 46 separate the individual combinations of IREDs and filters as well as preventing external light or radiation from impinging upon the sample. The drawing shows only five filters 26, 28, 30, 32 and 34 but in one preferred embodiment twelve filters are employed. These filters are conventionally available filters which have actual center response wavelengths which can vary over a tolerance range from their nominal center wavelengths of response.

In the present invention, it has been discovered that curvilinear interpolation techniques can be employed to acurately compute absorptivity values at additional nominal wavelengths from readings made using filters which have actual center wavelengths and bandwidths differing from described or nominal center wavelengths and bandwidths by normal tolerance. Additionally, calibration procedures can determine the precise nominal wavelengths in each instrument at which the computed absorptivity values are needed in the algorithms to accurately compute constituent percentages. This enables a reduction in the number of algorithm terms and measurement wavelengths necessary to compute constituent percentages since the need to compensate by additional algorithm terms and wavelength measurements is greatly reduced. Further, the employment of algorithms with single first and second derivative terms is enhanced since the absportivity values at the precise wavelengths necessary in such algorithms can be accurately computed. Accurate constituent percentages can now be determined in low cost instruments by algorithms with single optical data terms to produce substantial cost reductions in sample maintenance and analysis needed for calibration.

The optimum number of filters and their nominal center wavelengths of response can be determined by analysis of spectrum traces of the selected spectrum range. This can be done by computer analysis of accurate optical absorptivity data (log 1/T) which can be obtained from the precision scanning spectrophotometer of the United States Department of Agriculture (USDA) in Beltsville, Md. Beginning with the least practical number of filter wavelengths, every possible or practical combination of the practical number of wavelengths within the spectrum range is analyzed for suitability for accurate regeneration of the spectrum by curvilinear interpolation. The anlaysis at each practical or selected combination of wavelengths includes the mathematical generation of typical filter responses from the data (e.g., integration of a typical filter response function over a wavelength range to account for filter bandwidth at each selected wavelength), curvilinear interpolation of the generated filter responses to regenerate a spectrum trace, calculating the maximum deviation of the regenerated trace from the spectrophotometer data, comparing the maximum deviation with a previous least maximum deviation, and saving the wavelength combination data producing the least maximum deviation. This deviation analysis is preferably made for a variety of samples, for example four wheat samples containing high protein and high moisture, low protein and high moisture, high protein and low moisture, and low protein and low moisture, respectively. Additionally, the deviation analysis for each combination of wavelengths includes the deviations resulting when the center wavelength response and bandwidth varies within the nominal tolerance of the filter.

In one embodiment, the above analysis within a wavelength range from 900 to 1050 nanometers has determined that twelve filters having 10 nanometer half power bandwidths and center frequency responses of 918, 928, 940, 950, 968, 975, 985, 998, 1008, 1023, 1037 and 1045 nanometers with tolerance ranges of $\pm 2$ nanometers can be used to produce spectrum traces, by curvilinear interpolation, which do not exceed a maximum error of 0.00002 from USDA spectrophotometer traces which have one typical log 1/T value of 0.23156.

Positioned on the other side of the chamber 10 in front of the window 12 is a detector 56 for detecting light or infrared radiation transmitted through the sample S from the IREDs 16, 18, 20, 22 and 24 and filters 26, 28, 30, 32, and 34. Suitable arrangements (not shown) are provided to protect the detector 56 from receiving external light during measuring procedures. The output of the detector 56 is connected to a logarithmic amplifier circuit 58 which produces an output voltage proportional to the logarithm of the absorptivity (log 1/T) of the sample to the impinging infrared radiation.

Temperature sensors 48 and 49 are included for measuring the temperature of the grain sample being tested and the ambient temperature within the analyzer, respectively. Outputs of the sensors 48 and 49 are amplified by respective amplifiers 60 and 63 to present suitable voltages.

A sequence control or timing circuit 50, controlled by the microcomputer 54, has outputs connected to the corresponding IREDs 16, 18, 20, 22 and 24 for sequentially energizing the IREDs during the conducting of tests on the samples. Additionally, outputs of the timer 50 control a switching circuit 52 to connect the output of amplifier 58 to the input of an analog to digital converter 61 during the times that the IREDs are being pulsed, and to sequentially connect the outputs of amplifiers 60 and 63 to the input of the analog to digital converter 61 after the optical data readings are made so that sample temperature readings and ambient temperature readings are also made. The outputs of the analog to digital converter 61 are applied to inputs of the microcomputer 54. Suitable display and/or printer means 62 are connected to outputs of the computer 54.

Figure 2:
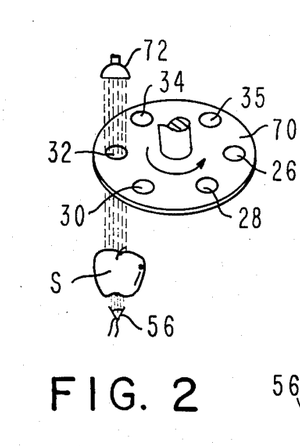
FIG. 2 is a diagram of a modified optical reading portion which can be substituted in the instrument of FIG. 1.
Figure 3:
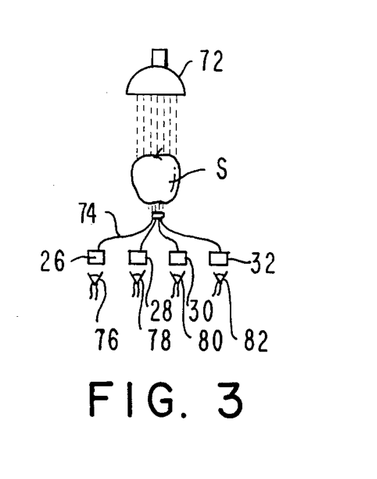
FIG. 3 is a diagram of a second modified optical reading portion which can be substituted in the instrument of FIG. 1.
Figure 4:
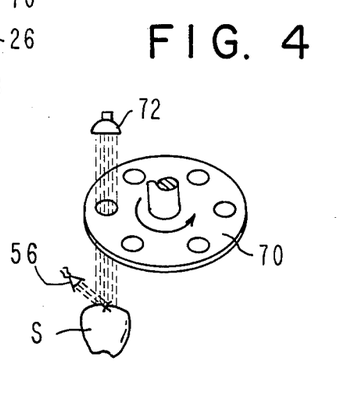
FIG. 4 is a diagram of a third modified optical reading portion which can be substituted in the instrument of FIG. 1.

In FIGS. 2, 3 and 4, there are shown three possible alternatives to the particular mechanism for obtaining sample readings. In FIG. 2, a disc 70 supporting the filters 26, 28, 30, 32, 34 and 35 rotate to sequentially pass light of the corresponding filter wavelength from light emitted by lamp 72 through sample S to detector 56; the sample S being illustrated as an apple and the detector 56 being positioned to detect light or radiation passing through the sample S. FIG. 4 utilizes the rotating filter disc 70 of FIG. 2 but positions the detector 56 so as to detect reflected light from the sample S. In FIG. 3, light from lamp 72 impinges directly on the sample S and transmitted light is divided by a fiber optic system 74 to apply portions of the light to the filters 26, 28, 30 and 32 which pass the corresponding wavelengths to detectors 76, 78, 80 and 82. The outputs of the detectors 76, 78, 80 and 82 will be amplified and connected by sequentially operated switching circuitry, similar to circuit 52 in FIG. 1, to the analog to digital converter 61 for being read by the computer 54.

Figure 5:
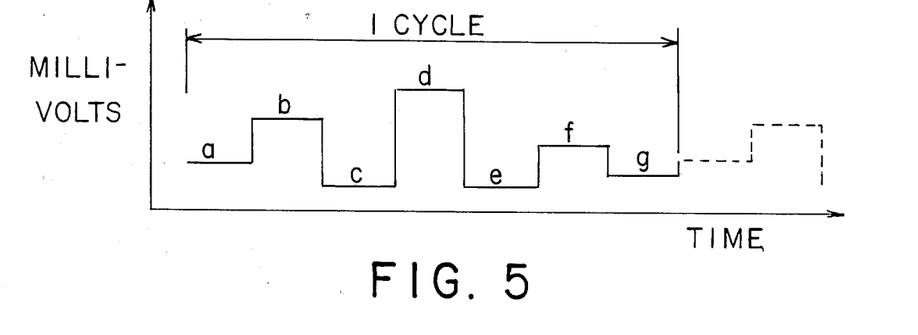
FIG. 5 is a waveform diagram of analog voltages applied to an analog to digital converter during a reading cycle in the instrument of FIG. 1.
Figure 7:
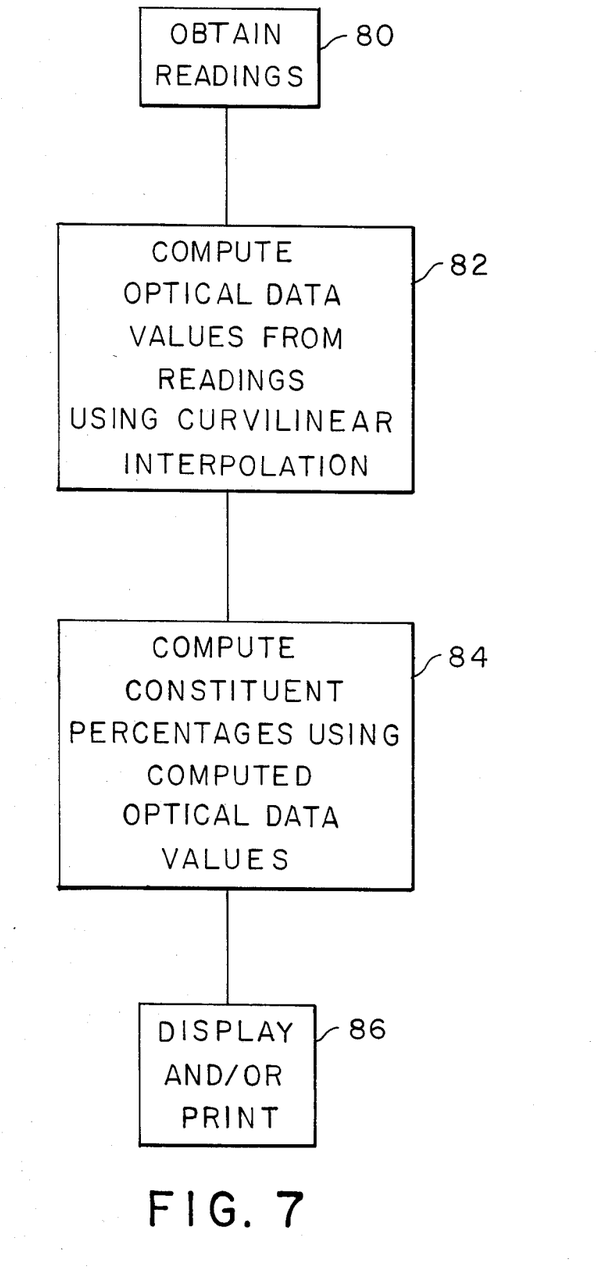
FIG. 7 is a flow diagram of a portion of a computer program for operating the instrument of FIG. 1.

The program for operating the computer 54, as shown in FIG. 7, includes steps 80, 82, 84, and 86. During the first step 80 optical data readings of the absorptivity of the samples are taken. As shown in FIG. 5, analog voltages or pulses a, b, c, d, e, f and g are applied to the input of the A/D converter 61 during a cycle of the timer 50. The outputs of the A/D converter 61 during each voltage pulse are read and stored in RAM of the microcomputer 54. The voltages a, b, c, d and e are proportional to the logarithm of the absorptivity of the sample of the corresponding wavelengths of infrared radiation passed by the filters 26, 28, 30, 32 and 34. Pulses f and g in FIG. 5 are the temperature readings from the respective thermisters 48 and 49.

In step 82, additional optical data values are computed using curvilinear interpolation techniques from the optical data values obtained in step 80. One typical curvilinear interpolation procedure using the Lagrange method is illustrated by the following program listing in BASIC computer langauge:

```
1010    FOR H=1 TO M
1020    OD(H)=0
1030    FOR J=1 TO P
1040    T=1
1050    FOR I=1 TO P
1060    IF I=J THEN 1080
1070    T=T * (SF(H)-F(I)) / (F(J)-F(I))
1080    NEXT I
1090    OD(H)=OD(H) + T * V(J)
1100    NEXT J
1110    NEXT H
```

Wherein
P = number of optic data readings made in step 80,
V(1) through V(P) = values of optical data readings made in step 80,
F(1) through F(P) - nominal response wavelengths of filters used for the readings in step 80
M = number of optical data values to be calculated,
SF(1) through SF(M) =0 wavelengths at which optical data values are to be calculated, and
OD(1) through OD(M) = new calculated optical data values.

In the next step 84, the percentages of the constituents of the sample are computed from the optical data values computed in step 82, measured values from step 80 are used when at the correct wavelength. For example, the percentage protein in a grain sample may be computed by the following algorithm:

$$\% \text{ protein} = K_o + K_1 \frac{d^2OD_1}{d^2OD_c} + K_2T_G + K_3T_A \quad (9)$$

Wherein
$T_G$ equals the temperature of the grain sample, $T_A$ equals the ambient temperature of the instrument, and $K_O$ through $K_3$ are constants derived by multiple regression techniques during calibratrion of the instrument.

$d^2OD_1$ and $d^2OD_c$ are second derivatives which are computed according to formula (7) from optical data values computed in step 82.

Alternatively, one of the above formulas (1), (2), (3) or (4) to which the linear temperature terms have been added could be utilized to compute the percentage protein.

Similar algorithms, but with different constants and using $OD_1$ and $OD_c$ at different wavelengths are utilized to compute percentage water, percentage fat, percentage starch, or other constituents.

After the desired constituent percentages have been calculated in step 84, these values are displayed and/or printed in step 86.

Figure 6:
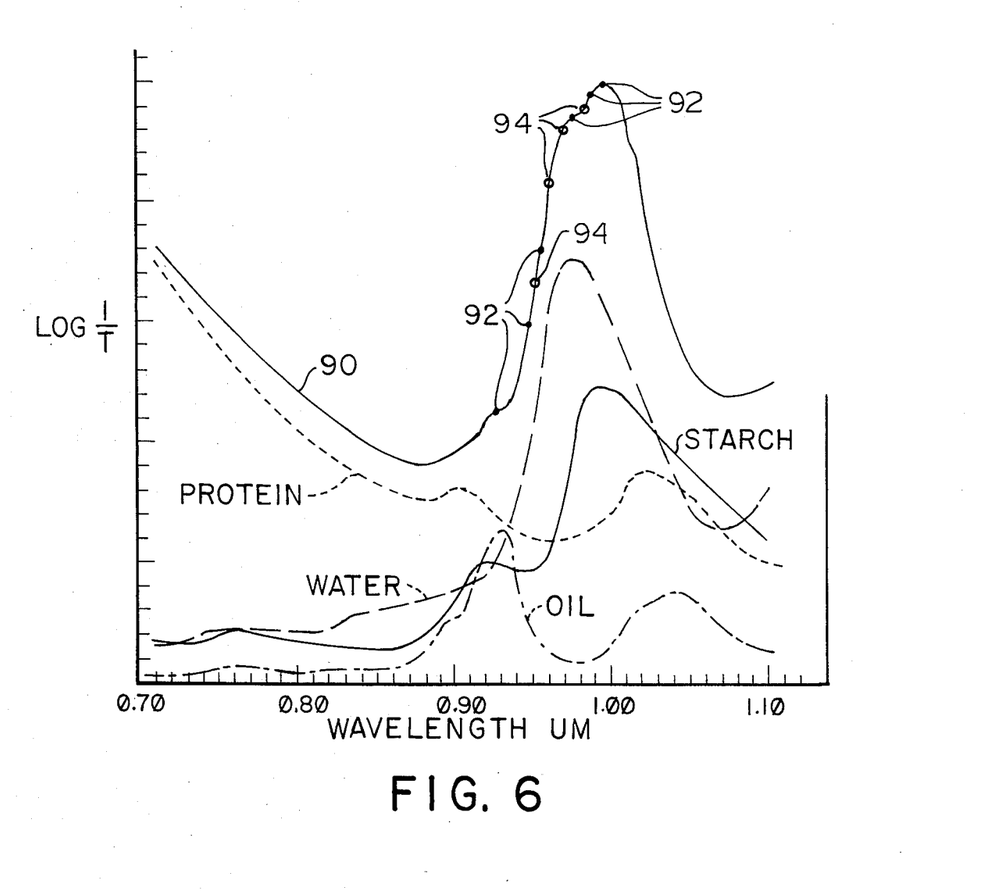
FIG. 6 is a curve diagram illustrating total absorptivity and constituent absorptivity of a grain sample over a portion of the near infrared wavelength spectrum.

Curve 90 in FIG. 6 illustrates the absorptivity of a wheat sample for a selected portion of the near infrared wavelength spectrum. Readings are made, for example, at points 92 along the curve 90. The actual wavelengths at which the readings 92 are made will vary from instrument to instrument due to variations of the actual center wavelengths from the nominal center wavelengths of the filters used to produce the corresponding readings. These readings may or may not correspond to the wavelengths at which optical data values are desired in order to compute the constituent percentages. Then additional optical data values 94 are computed by computer 54 utilizing curvilinear interpolation. These computed values are made at nominal wavelengths which are selected to be at the desired nominal wavelengths needed for computing the constituent percentages. The selected wavelengths may be at evenly closed spaced intervals to give a complete wavelength spectrum of absorptivity or may be made only at desired selected wavelengths necessary for computing the constituent percentages.

The absorptivity at any point on the curve 90 generally depends upon the values of two or more of the constituents, water, protein, oil and starch, but the absorptivity values at different wavelengths is contributed to in different proportions by the different constituents. In the prior art, absorptivity is measured at a sufficiently large number of different wavelengths contributed to in different proportions to insure accurate results; about twelve different readings have been necessary in use of algorithm (1) in this region of the spectrum. The necessity for a large number of different readings is due in part to the fact that tolerance variations in filter center bandwidth wavelength and the difference in readings resulting therefrom needs to be compensated for by readings at other wavelengths. Further, this filter wavelength variation substantially hinders or prevents use of formulas (3) and (5) with single first and second derivative terms at certain particularly interesting wavelengths; the second derivative formula (5) is particularly affected by this wavelength tolerance variation since the most interesting points are the absorptivity peaks of constituents where slight wavelength variations produce large second derivative variations.

The algorithm constants and the nominal wavelengths at which optical data values are used in the algorithms in step 84, are individually selected and incorporated in each instrument in the computer program or a memory table within ROM or preferably EE- PROM or RAM (with battery backup) so that the instrument can be readily recalibrated. The optimum constants and wavelengths can be selected by an optimization procedure in a general purpose calibration computer. A number of samples with varying constituents and temperatures are used to produce a corresponding number of sets of optical data readings from the assembled IREDs, filters, sensors and electronic circuitry of the instrument being constructed. These sets of data readings are used by the calibration computer to produce corresponding spectrum traces by curvilinear interpolation wherein each spectrum trace includes computed optical data values for each integer wavelength in the spectrum range. Also constituent percentages of the samples as accurately determined by analytical laboratory procedures are entered into the calibration computer. Each practical set of wavelengths is sequentially selected and analyzed for suitability in calculating each of the percentage constituents. This analyzation of each wavelength set includes computing the sets of constants for each set of wavelengths by a regression algorithm using the analytical constituent data and the computed optical data values, computing constituent percentages from the computed optical data values at the selected wavelengths, computing standard deviation of the computed constituent percentages from the analytical constituent percentages, comparing this standard deviation with the deviation of the best previous wavelength set, and saving the constant values and wavelength data for the wavelength sets with the least deviation.

In one preferred embodiment utilizing about forty samples and algorithms (7) and (9), the above step of sequentially selecting each practical set of wavelengths is performed by first selecting a set of arbitrary wavelengths for the denominator of algorithm (9). Sets of wavelengths for the numerator of algorithm (9) are then sequentially selected to determine optimum numerator wavelengths for the selected denominator wavelengths. The denominator wavelengths are then sequentially selected to determine optimum selected denominator wavelengths for the previously determined optimum numerator wavelengths. Then the above steps for sequentially selecting numerator and denominator wavelengths are repeated several times until the optimum wavelengths remain the same to indicate that optimum wavelengths have been found.

The best optimum sets of wavelengths and constants are then incorporated into the computer memory of the instrument being constructed. The calculated best wavelengths and constants will vary from instrument to instrument due to normal variations of actual wavelength of response and electrical component values from nominal filter wavelengths and component values. For example, best wavelengths for calculating percentage water in wheat samples by algorithms (5) and (7) in two separate instruments using twelve filters with the same nominal wavelength responses were found as follows in Table I:

TABLE I

| WAVELENGTHS FOR ALGORITHM (5) | | |
|---|---|---|
| | Instrument 1 | Instrument 2 |
| Numerator algorithm | $W_1=970$ nm | $W_1=972$ nm |
| | $W_2=950$ nm | $W_2=949$ nm |
| | $W_3=990$ nm | $W_3=995$ nm |
| Denominator algorithm | $W_1=956$ nm | $W_1=954$ nm |
| | $W_2=931$ nm | $W_2=930$ nm |

TABLE I-continued

| WAVELENGTHS FOR ALGORITHM (5) | |
|---|---|
| Instrument 1 | Instrument 2 |
| $W_3=981$ nm | $W_3=978$ nm |

If the instrument is being constructed to analyze different types of grain (wheat, soybeans, barley, oats, corn, rye, etc.), then the calibration procedure is repeated for each grain.

The employment of curvilinear interpolation techniques to produce accurate absorptivity values at a number of nominal wavelengths can be advantageously used in many additional ways. For example, temperature changes in a sample under test can produce a shift in an absorption peak for a constituent to different wavelengths; the algorithm computation wavelength can readily be changed in accordance with the measured grain temperature to compensate for this absorption peak shift. In another example, different types of grain can have different optimum algorithm computation wavelengths; such different computation wavelengths can be readily selected in the ROM program or by switch means to enable the manufacture of universal instruments without requiring a large number of different wavelength responsive filters.

Since many modifications, variations and changes in detail can be made in the above-described embodiments, it is intended that all matter described above and shown in the accompanying drawings be interpreted as illustrative and not in a limiting sense.

What is claimed is:

1. An apparatus for optically obtaining a quantitative value of a constituent having a wavelength variable optical absorptivity in a sample, comprising:
    means for measuring optical absorptivity of a sample at a plurality of predetermined different wavelengths to obtain a corresponding plurality of measured optical absorptivity values,
    means for computing a plurality of computed optical absorptivity values by a curvilinear interpolation technique from the measured optical absorptivity values, and
    means for computing the constituent quantitative value from optical absorptivity values including one or more of the computed optical absorptivity values.

2. An apparatus as claimed in claim 1 wherein the means for computing the constituent quantitative value includes means for computing a derivative of an optical absorptivity value at a selected wavelength using one or more of the computed optical absorptivity values.

3. An apparatus as claimed in claim 2 wherein the means for computing the derivative includes means for computing a second derivative of the computed optical absorptivity value at the selected wavelength.

4. An apparatus as claimed in claim 1 wherein the means for measuring optical absorptivity includes means for generating radiant energy, detecting means for detecting radiant energy transmitted or reflected from the sample., and a plurality of narrow bandpass filters for being interposed in one or more like optical paths between the radiant energy generating means and the detecting means to thus correspondingly generate the plurality of measured optical absorptivity values from the detecting means.

5. An apparatus as claimed in claim 4 wherein the means for computing the constituent quantity from the optical absorptivity values includes means for computing a derivative of an optical absorptivity value at a selected wavelength using one or more computed optical absorptivity values.

6. An apparatus as claimed in claim 5 wherein the means for computing the derivative includes means for computing the second derivative of the computed optical absorptivity value at the selected wavelength.

7. An apparatus as claimed in claim 4 wherein the means for generating radiant energy includes means for generating near infrared energy, and the plurality of narrow bandpass filters includes a plurality of filters having center bandpass wavelengths in the near-infrared spectrum.

8. An apparatus as claimed in claim 7 wherein the plurality of filters includes twelve filters having nominal center bandpass wavelengths of 918, 928, 940, 950, 968, 975, 985, 998, 1008, 1023, 1037 and 1045.

9. An apparatus as claimed in claim 1 wherein the means for computing the constituent quantitative value includes memorized indications of nominal wavelengths which have been determined by calibration to have optical absorptivity values which produce least deviating constituent quantitative values using a selected algorithm, and means using the selected algorithm and the optical absorptivity values corresponding to the memorized indications to compute the constituent value.

10. A method of optically obtaining a quantitative value of a constituent having a wavelength variable optical absorptivity in a sample, comprising the steps of:
measuring optical absorptivity of the sample at a plurality of predetermined different wavelengths to obtain a corresponding plurality of measured optical absorptivity values,
computing a plurality of computed optical absorptivity values by a curvilinear interpolation technique from the measured optical absorptivity values, and
computing the constituent quantitative value from optical absorptivity values including one or more of the computed optical absorptivity values.

11. A method as claimed in claim 10 wherein the step of computing the constituent quantitative value includes computing a derivative of an optical absorptivity value at a selected wavelength using one or more of the computed optical absorptivity values.

12. A method a claimed in claim 11 wherein the step of computing the derivative includes computing a second derivative of the optical absorptivity value at the selected wavelength.

13. A method as claimed in claim 10 wherein the step of measuring optical absorptivity includes generating radiant energy impinging on the sample, detecting radiant energy transmitted or reflected from the sample, and sequentially filtering the radiant energy by a plurality of narrow bandpass filters interposed in one or more optical paths between the radiant energy generating means and the detecting means to thus correspondingly generate a plurality of measured optical absorptivity values from the detecting means.

14. A method as claimed in claim 13 wherein the step of computing the constituent quantity from the optical absorptivity values includes computing a derivative of an optical absorptivity value at a selected wavelength using one or more of the computed optical absorptivity values.

15. A method as claimed in claim 14 wherein the step of computing the derivative includes computing the second derivative of the optical absorptivity value at the selected wavelength.

16. A method as claimed in claim 13 wherein the step of generating radiant energy includes generating near infrared energy, and the filtering step includes filtering by a plurality for filters having center bandpass wavelengths in the near-infrared spectrum.

17. A method of calibrating an apparatus for optically obtaining a quantitative value of a constituent having a wavelength variable optical absorptivity in a sample, wherein the apparatus includes an assembly of (a) radiant energy source means for impinging upon the sample, (b) means for detecting radiant energy transmitted or reflected from the sample, (c) a plurality of narrow bandpass filters for being interposed in one or more optical paths between the radiant energy source means and the detecting means, and (d) computer means including a memory for analyzing a plurality of output values of the detecting means corresponding to the respective filters wherein the number and nominal center response wavelengths of the filters have been selected so that curvilinear interpolation of absorptivity data reading corresponding to the filters generates absorptivity data spectrum traces with less than a predetermined deviation from measured absorptivity data spectrum traces; the method comprising the steps of:
obtaining absorptivity data readings corresponding to the filters from the assembled (a), (b) and (c) for a plurality of samples;
generating a plurality of wavelength spectrum traces of absorptivity data values corresponding to the plurality of samples by curvilinear interpolation from the obtained data readings;
selecting wavelengths at which the optical data values, when utilized in an algorithm, produce the least deviation in computed constituent percentages of the samples from actual measured constituent percentages; and
incorporating indications of the selected wavelengths into the computer memory to thereby enable the computer to utilize the algorithm to accurately compute constituent percentages.

18. A method as claimed in claim 17 wherein the step of selecting wavelengths includes selecting each practical set of wavelengths, computing constituent percentages by the algorithm for the samples at each selected set of wavelengths, determining a deviation of constituent percentages at each selected set of wavelengths, comparing each determined deviation with a previously least deviation, and saving the corresponding set of wavelengths and least deviation found by the comparing.

* * * * *

UNITED STATES PATENT AND TRADEMARK OFFICE
CERTIFICATE OF CORRECTION

PATENT NO. : 4,627,008

DATED : December 2, 1986

INVENTOR(S) : Robert D. Rosenthal

It is certified that error appears in the above-identified patent and that said Letters Patent is hereby corrected as shown below:

Column 2, line 56, "$K_A K_A$", should be --$K_A T_A$--.

Signed and Sealed this

Twenty-fourth Day of February, 1987

Attest:

DONALD J. QUIGG

Attesting Officer     Commissioner of Patents and Trademarks